United States Patent [19]

Smith et al.

[11] Patent Number: 4,741,337

[45] Date of Patent: May 3, 1988

[54] SURGICAL FASTENER MADE FROM GLYCOLIDE-RICH POLYMER BLENDS

[75] Inventors: Carl R. Smith, Bloomingdale; Mark T. Gaterud, Annandale; Dennis D. Jamiolkowski, Long Valley; Hugh D. Newman, Jr., Chester; Shalaby W. Shalaby, Lebanon, all of N.J.

[73] Assignee: Ethicon, Inc., Somerville, N.J.

[21] Appl. No.: 755,888

[22] Filed: Jul. 17, 1985

[51] Int. Cl.[4] .................. A61B 17/04; A61B 17/08
[52] U.S. Cl. ..................... 128/334 R; 128/334 C; 128/325; 128/326; 128/335.5; 525/410; 525/415
[58] Field of Search .............. 128/334 C, 334 R, 325, 128/326, 335.5, 92 R, 92 BB, 346, 337; 227/DIG. 1; 525/410, 415; 528/354; 604/891

[56] References Cited

U.S. PATENT DOCUMENTS

| | | | |
|---|---|---|---|
| 3,839,297 | 10/1974 | Wasserman et al. | 260/78.3 R |
| 3,892,821 | 7/1975 | Koleske et al. | 260/860 |
| 4,137,921 | 2/1979 | Okuzumi et al. | 128/335.5 |
| 4,214,586 | 7/1980 | Mericle | 128/334 R |
| 4,402,445 | 9/1983 | Green | 128/334 C |
| 4,523,591 | 6/1985 | Kaplan et al. | 128/334 R |
| 4,532,926 | 8/1985 | O'Holla | 128/334 C |
| 4,534,350 | 8/1985 | Golden et al. | 128/334 C |
| 4,579,118 | 4/1986 | Failla | 128/325 |
| 4,605,730 | 8/1986 | Shalaby et al. | 128/335.5 |

Primary Examiner—Richard J. Apley
Assistant Examiner—Paul Prebilic
Attorney, Agent, or Firm—Charles J. Metz

[57] ABSTRACT

A surgical fastener is made from a glycolide-rich blend of polymers.

8 Claims, 4 Drawing Sheets

SURGICAL FASTENER MADE FROM GLYCOLIDE-RICH POLYMER BLENDS

The invention relates to an absorbable surgical fastener such as a ligating clip or a surgical staple of the staple/receiver type, made from glycolide-rich blends of polymers.

BACKGROUND OF THE INVENTION

Surgical staples and ligating clips are beginning to come into wide use in the surgical profession as an alternative to sutures and ligatures. One advantage of clips and staples in comparison with sutures and ligatures is that tissue fastening or ligating with a staple or clip, whether applied singly or as an array applied in a row or in a ring, is much simpler and faster than with a suture or a ligature. Surgical procedures can be speeded up, thereby reducing the length of time the patient must be anesthetized and shortening the operating room time. Thus, there are both medical and economic reasons for the shift to staples and clips from sutures and ligatures.

The first surgical staples to be used, and still the majority being used, were metal staples. But metal staples, when used externally, must be removed, with accompanying patient discomfort. And when metal staples are used internally, they are left in place. While the metal staples are tiny and become encapsulated by natural processes, and little or no difficulty has been associated with such staples left in the patient, for internal applications, surgeons would prefer to use absorbable materials that eventually disappear after their usefulness has ended. For this reason, there is a substantial incentive to develop an absorbable plastic surgical staple.

It appears to be out of the question to produce an absorbable plastic surgical staple of reasonable size that fastens simply by bending back on itself in a manner analogous to the way metal staples fasten. The available absorbable plastics simply lack the required combination of ductility and stiffness that would be required for this purpose. For this reason, the initial attempts to produce an acceptable absorbable plastic surgical staple has concentrated on the staple/receiver type of fastener. In this type of fastener, a staple member includes a crosspiece or base and one or more attached legs which are designed to pierce the tissue to be fastened and to enter receptacles in the receiver on the other side of the tissue. The receiver holds the legs tightly, with the tissue being held between the cross-piece or base and the receiving member. The desirable characteristics of such a fastener are the following:

(1) adequate stiffness in the legs to pierce the tissue without being deflected in such a way that they fail to meet the receptacles in the receiver;
(2) adequate strength in the receiver to hold the legs;
(3) strength retention in vivo for a period which may vary from about three to six weeks, depending on the function of the fastener;
(4) dimensional stability at moderately elevated temperatures, e.g., up to 65° C.;
(5) sterilizability; and
(6) ability to be totally absorbed or at least nonpalpable within a reasonable period of time.

It has not proven to be an easy matter to obtain the requisite combination of properties. For instance, early designs of absorbable surgical staples utilized temporary metal reinforcement for the fastener legs during insertion of the staple to insure adequate stiffness. For instance see Noiles, U.S. Pat. No. 4,060,089 and Green, U.S. Pat. No. 4,402,445. A presently commercial absorbable clip and an early commercial absorbable staple are made from an 80/20 lactide/glycolide (mol/mol) copolymer. These fasteners have the disadvantage that they are dimensionally unstable when heated to temperatures over 120° F. (49° C.). Therefore, care must be taken in handling these fasteners, because temperatures well over 120° F. are commonly encountered in shipping and storage in the United States during the warmer months.

Later commercial surgical staples are made from either of two blends of lactide and glycolide polymers such that in each case the blend has greater than 50 per cent lactide-based moieties. Specifically, one blend had an overall lactide/glycolide ratio of 71/29, by weight, and the other, 64/36, by weight.

Absorbable ligating clips made from poly(p-dioxanone) have recently been introduced commercially. Metallic ligating clips have been used for some time.

This invention provides an absorbable surgical fastener, such as a surgical staple, a ligating clip, an anastomotic coupler, a fascia closure, or the like, that has an overall composition containing more than 50 per cent of polymerized glycolide, and provides, unexpectedly, a highly desirable combination of properties. With such a high glycolide content, one would have expected the subject devices to have limited strength retention in vivo; polyglycolide (homopolymer) staples have an unacceptable strength retention profile in that they lose their strength in an unacceptably short period of time for most surgical uses. However, the staples and other devices of this invention do retain a substantial proportion of their initial strength during the critical wound healing period.

BRIEF SUMMARY OF THE INVENTION

This invention provides a surgical fastener comprising a glycolide-rich blend of polymers. In one preferred aspect the invention provides a surgical staple comprising:

(a) a staple member including a base member and at least one pointed leg member extending substantially perpendicularly from said base member; and
(b) a receiving member including an aperture arranged and constructed to receive and retain the free end of said leg member, wherein said staple member comprises a glycolide-rich blend of polymers, and wherein said receiving member comprises an absorbable polymer, such as poly(p-dioxanone) or a glycolide-rich blend of polymers.

In another preferred aspect, the invention provides a hemostatic ligating clip comprising said glycolide-rich blend of polymers.

Among the advantages of the invention are the ability to injection mold the parts made from the blend of the invention, and the fact that the parts retain measurable strength for a long enough time after implantation to perform the required task, and yet the parts become nonpalpable only six to ten weeks after implantation in living tissue. This latter feature is a truly valuable and unexpected advantage.

THE PRIOR ART

Green, in U.S. Pat. No. 4,402,445, discloses absorbable surgical staples made from, inter alia, "an amorphous copolymer of 10–50% (by weight) glycolide and 50–90% lactide . . . " and from " . . . polymers of p-dioxanone . . . " Noiles, in U.S. Pat. No. 4,060,089, discloses the preparation of surgical staples from polyglycolic acid and polylactic acid.

Mericle, in U.S. Pat. No. 4,428,376, discloses the preparation of surgical staples from homopolymers and copolymers of lactide, glycolide, and p-dioxanone.

Golden et al., in U.S. Pat. application Ser. No. 359,443, filed Mar. 18, 1982, discloses an absorbable staple in which the fastening member is made from "an absorbable polymer of glycolide and lactide" and the receiving member is made from poly(p-dioxanone). The said Golden et al. application is assigned to the same assignee as this application.

Doddi et al., in U.S. Pat. No. 4,052,988, disclose surgical devices made from poly(p-dioxanone).

World patent application No. WO8401-508-A describes absorbable surgical fasteners made from copolymers containing 70–85 mole per cent lactide and 15–30 mole per cent glycolide.

DETAILED DESCRIPTION OF THE INVENTION

Figure 1:
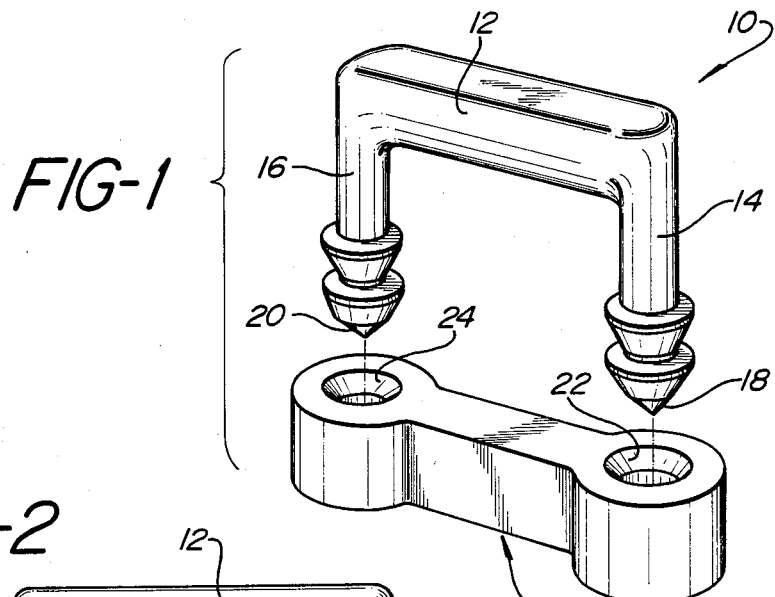
FIG. 1 is an exploded perspective view of a staple/receiver type surgical staple useful in the invention.

The invention resides in the use in a surgical fastener of a blend of at least two polymers, the overall blend being rich in polymerized glycolide.

The blend of polymers used in the invention is glycoliderich, that is, the blend as a whole contains from about 65 to about 85 weight per cent polymerized glycolide, the remainder being polymerized lactide. At least one of the polymers in the blend is polyglycolide homopolymer or a predominantly glycolide copolymer containing, e.g., at least about 90 mole per cent glycolide, the remainder being lactide. Also, at least one of the polymers in the blend is polylactide homopolymer or a predominantly lactide copolymer containing, e.g., at least 85 mole per cent lactide, the remainder being glycolide. The two or more polymers used in the blend are used in such proportions that, overall, the blend contains from about 65 to about 85 weight per cent of polymerized glycolide, the remainder being polymerized lactide.

The polymers used in the invention are known materials. For instance, they are disclosed in U.S. patents to Schneider (No. 3,797,499), Salzberg (No. 2,758,987), and Schmitt et al. (No. 3,739,773). As a rule, the lactide hompolymers and lactide-rich copolymers will have molecular weights such that they have inherent viscosities of from about 1 to about 3 and preferably about 1.5 to 1.9, dl/gm, tested at 25° C. at a concentration of 0.1 gm/dl in hexafluoroisopropyl alcohol ("HFIP"). The glycolide homopolymers and glycolide-rich copolymers are easier to characterize by melt index than by inherent viscosity because of their poor solubility in organic solvents. They usually have melt index values of from about 0.1 to about 0.9, and preferably from about 0.2 to about 0.6, gram per 10 minutes. The melt index is determined by the procedure described in ASTM D 1238-73 (using a thoroughly dried sample of polymer), using a 26 mil die orifice, a weight of 3700 grams plus the 100-gram piston weight, at a temperature of 235° C. The melt index is the weight of polymer taken during the interval from 15 to 16 minutes after beginning the test, multiplied by 10.

Poly(p-dioxanone), one preferred polymer for use in the receiver member of a surgical staple of the staple/receiver type, is also a known material. Its nature and preparation are described, for instance, in Doddi et al., U.S. Pat. No. 4,052,988. Poly(p-dioxanone) having an inherent viscosity of from about 1.2 to about 2.2, and preferably about 1.6 to 1.9, dl/gm, tested at 25° C. and a concentration of 0.1 gm/dl in HFIP, is normally used in the receiver. The blend of the invention may also be used as the receiver.

In one preferred aspect, the invention provides a surgical staple of the staple/receiver type wherein the staple member is the blend of the invention and the receiver is an absorbable polymer, such as poly(p-dioxanone) or a blend similar to or the same as that used in the staple member.

The staple can be made by injection molding of the two parts. The staple member, which is made of a blend of two or more polymers, can be injection molded at temperatures within the range of from about 215° C. to about 225° C. at an injection molding pressure of, for example, 1650 to 1750 psi. (These conditions are typical for the preferred 70/30 polyglycolide/polylactide blend disclosed in the Examples below.) These conditions are also used if the blend is used as the receiver. Typically, the feed for the injection molder will be a melt blend of the polymers in pellet form, although a dry blend of the polymers in finely divided form can be fed to the injection molding machine, provided sufficient mixing in the injection molding machine occurs. The receiver member, when made of poly(p-dioxanone), can be injection molded at a temperature within the range of from about 105° C. to about 120° C., at a pressure of, for example, about 1350 to 1450 psi. The polymers should be quite dry when being injection molded in order to avoid hydrolytic degradation during processing. After molding, the staple can be packaged and sterilized by conventional procedures.

It is recommended that the polymers be handled so as to minimize premature hydrolytic degradation or thermal degradation. Thus, the polymers should be stored dry before molding, the molding operation should be dry, and the molded parts should be stored dry. Also, residence time during processing should be kept to a minimum so as to minimize thermal and shear degradation.

Figure 2:
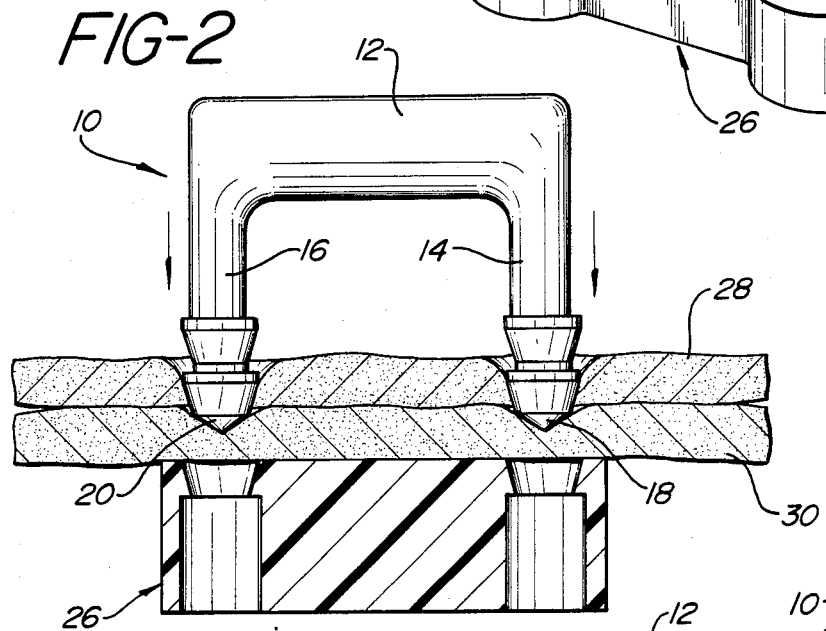
FIG. 2 is a front view of the staple of FIG. 1 in the act of fastening tissue.
Figure 3:
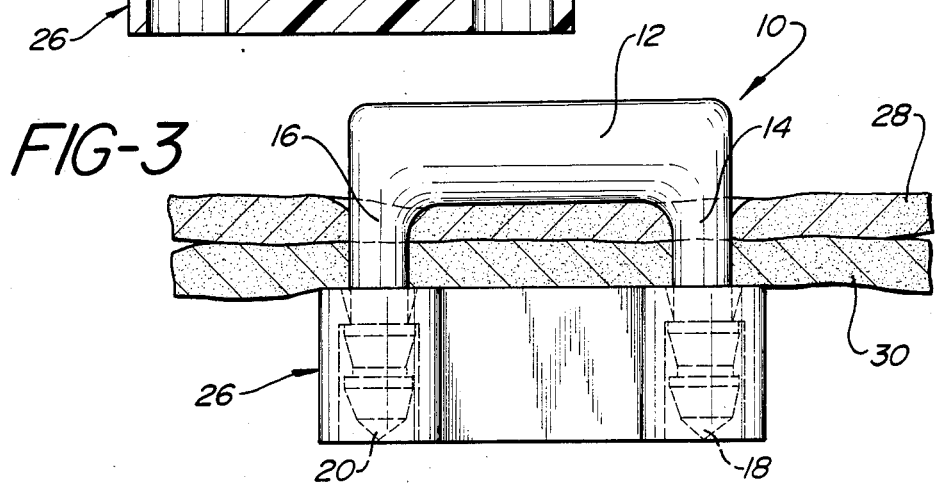
FIG. 3 is a front view of the staple of FIG. 1 in place holding tissue together.

FIGS. 1–3 show a typical surgical staple of the invention. The staple member 10 includes a base 12 and two legs 14,16 extending generally perpendicularly from the base 12. Each leg 14,16 has a pointed end 18,20 that is capable of piercing tissue. The legs 14,16 are arranged and constructed so as to snap fit into the receptacles 22,24 of a receiver 26. In a typical use, layers 28,30 of tissue to be fastened are positioned between the staple member 10 and the receiver 26. The legs 14,16 of the staple member 10 are driven through the layers 28,30 of tissue, as shown in FIG. 2, until the ends of the legs 14,16 snap fit in the receptacles 22,24 in the receiver 26, to thereby hold the tissue securely between the staple member 10 and receiver 26, as is shown in FIG. 3. The design of staple member and receiver shown in the figures is merely illustrative. Other designs can be used, if desired.

In another preferred aspect of the invention, there is provided a hemostatic ligating clip comprising the blend of the invention. The advantages of the clip comprising the blend of the invention compared to clips made wholly of poly(p-dioxanone) are the following:
(a) more rapid absorption by the body; and
(b) the blend is stiffer, so a clip made from the blend would more readily be able to penetrate tissue.

Figure 4:
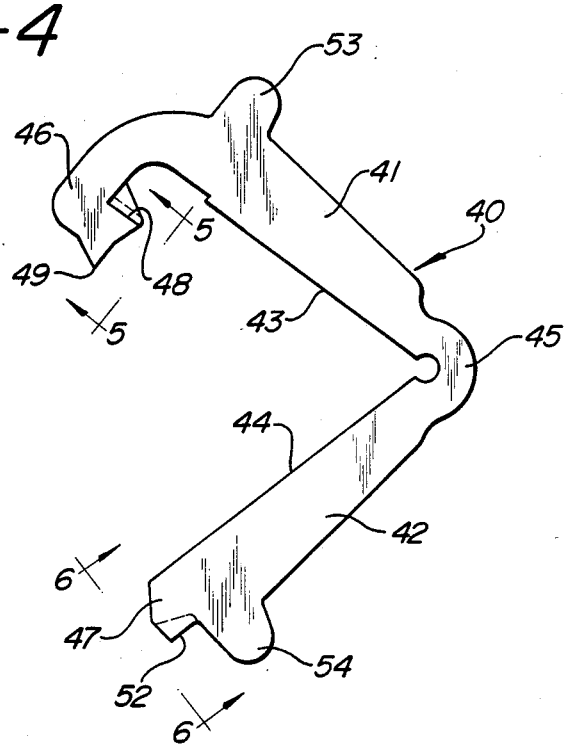
FIG. 4 is a perspective view of a ligating clip useful in the invention.

Referring to the drawings (FIGS. 4-9), there is shown a clip 40 that can be used in the invention. As depicted in FIG. 4, the clip comprises a pair of leg members 41 and 42 having opposed vessel clamping surfaces 43 and 44. The leg members are connected at their proximal ends by a resilient hinge portion 45.

Figure 5:
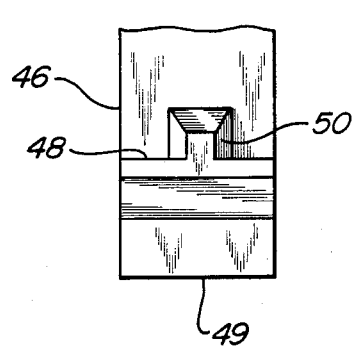
FIG. 5 is a front view taken along line 5—5 of FIG. 4.
Figure 6:
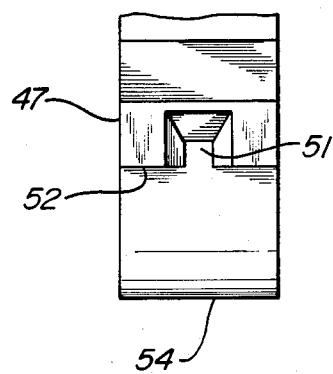
FIG. 6 is a front view taken along line 6—6 of FIG. 4.

The distal end of one of the leg members terminates in a return bend hook portion 46. The opposite leg member is somewhat shorter and terminates at its distal end in a portion 47 which can be grasped by the hook portion. The end of this leg member is angled at an obtuse angle to the vessel clamping surface. This angle aids in deflecting the hook portion as the two leg members are brought together about the hinge and allows the hook portion to deflect and then accept the leg member in the area between the inner surface 48 of the hook portion and the vessel clamping surface 43 of the opposite leg member. The hook portion includes a sharpened pointed end 49 extending from the hook portion and positioned to lead the hook portion or preceed the hook portion as the clip is being closed. As shown in FIG. 5, the hook portion has a protrusion 50 disposed from the central portion of its inner surface 48. This protrusion fits into the recess 51 (see FIG. 6) positioned in the outer surface 52 of the opposite leg member 42. The protrusion and recess interlock when the clip is closed to prevent lateral movement of the leg members. The outside surfaces of the leg members each include a cylindrical boss 53 and 54 for use in holding the clip in a suitable instrument and applying the clip from said instrument as will hereinafter be described.

Figure 7:
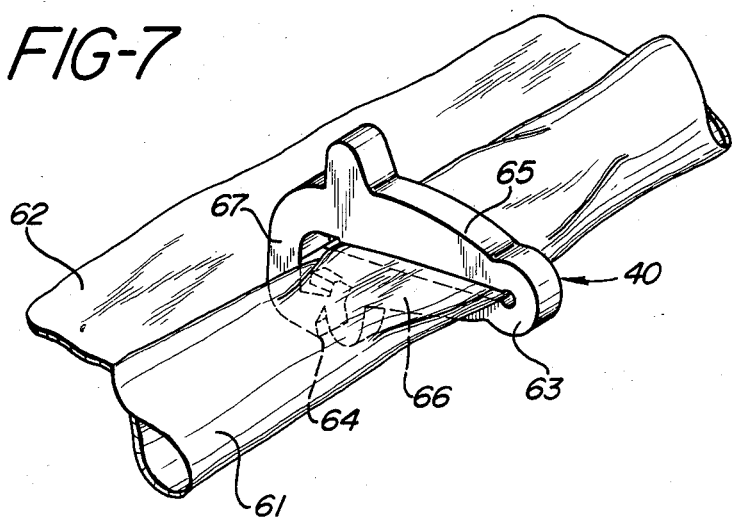
FIG. 7 is a perspective view of the clip depicted in FIG. 4 in a closed position about a blood vessel.
Figure 8:
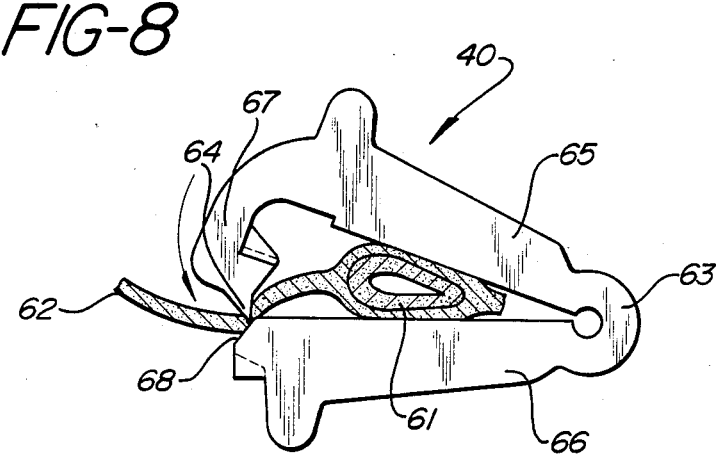
FIG. 8 is a side view of the clip of FIG. 4 immediately prior to the clip being closed about a vessel to be ligated.
Figure 9:
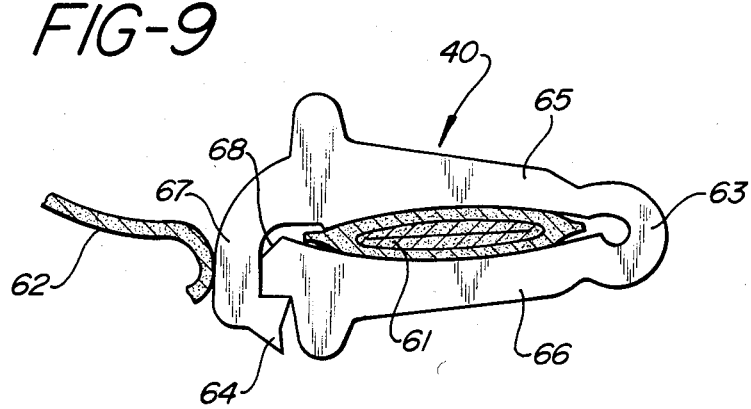
FIG. 9 is a side view of the clip of FIG. 4 with the clip in the fully closed position.

As may be more clearly seen in FIGS. 7, 8, and 9, when the clip 40 is clamped about a vessel 61 to be closed, assuming that the vessel has not been fully dissected from the surrounding connective tissue 62 (such as would be found in the mesentary), the vessel clamping surfaces are placed on opposite sides of the vessel and the leg members urged together about the resilient hinge. The penetrating sharpened end 64 of the one leg member 65 will pinch and scrape the connective tissue between itself and the camming surface 68 of the other leg member 66. This scraping action enhances the tissue penetrating ability of the sharpened end. Once the tissue is penetrated the usual sequence of closure takes place. As the leg members are urged closer together the leg member 66 continues to deflect the hook portion 67 and becomes engaged by the leg member 65, thereby locking the clip in place about the vessel without tissue interference with latch security. Though in the embodiment shown the penetrating means is a sharpened beveled end, the penetrating means may have other configurations such as a pointed end tapered at a plurality of sides, a pointed end, a plurality of pointed ends, etc.

Figure 10:
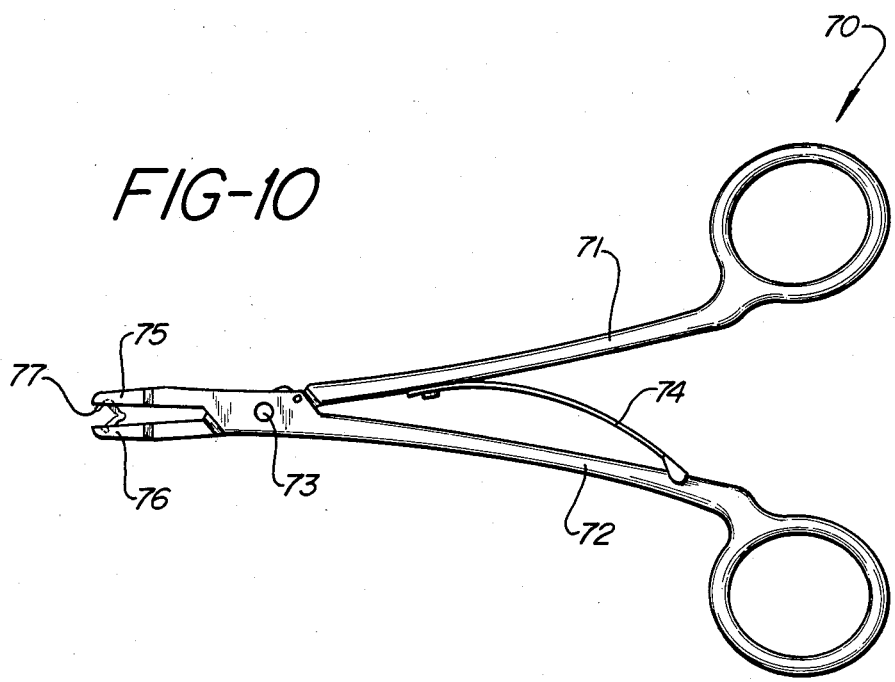
FIG. 10 is a side view of one type of instrument that may be used in applying the clip of FIG. 1.

In FIG. 10, there is shown a simplified drawing of an instrument for applying the clip described above. This instrument 70 comprises a pair of handles 71 and 72 which are connected together at a hinge point 73. The handles are biased with respect to one another by a spring 74. One of the handles extends beyond the hinge point in a first jaw member 75 and the opposite handle extends beyond the hinge point in a complementary second jaw member 76. The instrument engaging means comprises cylindrical bosses (53, 54 in FIG. 4) extending from the back surfaces of the leg members of the clip 77. These bosses fit into recesses in the jaws of the instrument.

The clip is placed in the jaws with the cylindrical boses in the appropriate recesses. The vessel clamping surfaces of the clip are then placed on opposite sides of the vessel to be closed and the instrument handles urged together closing and locking the clip about the vessel and shutting off the vessel.

The clip can be injection molded by the procedure set forth above with respect to the staple member of the surgical staple of the invention.

After injection molding, the parts made of the blend of the invention can be annealed to enhance dimensional stability at elevated temperature. The annealing usually increases the degree of crystallinity. Polyglycolide homopolymer and glycolide-rich copolymers often develop crystallinity in the mold, and this degree of crystallinity may be sufficient in some cases. The parts made from the blend of the invention usually exhibit about 15 to about 45 per cent crystallinity, measured by X-ray diffraction. The annealing, which is preferably done in a vacuum or under an inert atmosphere such as dry nitrogen, can be carried out at about 50° to 140° C., and preferably at about 60° C. to 80° C., for at least an hour. An annealing time of about 2 to 20 hours is preferred.

EXAMPLES

Surgical staples having the design shown in FIGS. 1-3 were made by injection molding. The receivers were all made from poly(p-dioxanone) having an inherent viscosity of 1.6-1.8 in HFIP. The staple members were made from a blend of 70 parts by weight of polyglycolide homopolymer having a melt index 0.291, and 30 parts by weight of polylactide homopolymer having an inherent viscosity in HFIP of 1.78.

Prior to injection molding, the polymers, in coarse ground form, were dried under vacuum for a period of two weeks. They were dry blended and fed to the injection molding machine as a dry blend. Dryness was maintained during molding by using a dry nitrogen purge in the hopper of the injection molding machine. After molding, the samples were maintained under vacuum or under a dry nitrogen purge until they were tested. The fasteners were annealed at 60° C. for 16 hours after molding.

The fasteners of the invention maintain measurable holding strength in vivo for a period of time sufficient to enable joined tissue to heal. This is illustrated by the fact that in vitro testing in phosphate buffer, pH=7.27, at 37° C., of the fasteners reveals that the force to separate the receiver from the staple member is still measurable after 21 days.

The procedure for testing the separation force is the following:

An Instron Tensiometer is set as follows:

| Crosshead speed | 0.5 inch/minute |
|---|---|
| Chart speed | 5.0 inches/minute |
| Gauge Length | 1.5 inches |

Full scale load as follows:

| Time in days | Full Scale Calibrations |
|---|---|
| 0 | 10 pounds |
| 7 | 5 pounds |
| 14 | 5 pounds |
| 21 | 2 pounds |
| 28 | 2 pounds |

The staple members are inserted in the receivers, leaving a slight gap to simulate the space taken up by tissue, and are then placed in the phosphate buffer at 37° C. The samples are tested initially and after 7, 14, 21, and 28 days.

The separation force is measured by engaging the cross piece (e.g., part 12 in FIG. 1) of the staple member with a tab of an Instron test fixture, and pulling against a strip of polyester film that has been bent around the receiver by passing it through the gap between crosspiece of the staple member and the receiver. (The polyester film is cut so that it is just narrow enough to fit through said gap.) Typical initial separation forces vary from about 8 to 9 pounds, and typical separation forces after 21 days in phosphate buffer at 37° C. are from one-half to one pound.

After 42 days in vitro, the devices made from the blend described above are so soft that they would be expected to be non-palpable after 42 days in vivo. It is unusual and unexpected that an implanted device would have measurable strength after three weeks in vivo, but then after only another three weeks be so soft as to be non-palpable. In general, the fasteners of the invention will be non-palpable after six to ten weeks in vivo.

While the invention has been described most specifically in terms of a surgical staple or a hemostatic ligating clip, other types of surgical fasteners can be made from the blend of the invention. Such fasteners include fascia closures and anastomotic couplers.

What is claimed is:

1. A surgical fastener comprising a blend of at least two polymers, one of said polymers being polyglycolide homopolymer or a copolymer containing at least about 90 mole percent polymerized glycolide, the other of said polymers being polyactide homopolymer or a copolymer containing at least about 85 mole percent polymerized lactide, with the overall blend containing from about 65 to about 85 weight percent polymerized glycolide, the remainder being polymerized lactide, wherein the fastener comprising said blend is non-palpable after six to ten weeks in vivo.

2. The surgical fastener of claim 1 in the form of a surgical staple comprising:
   (a) a staple member including a base member and at least one leg member terminating in a pointed free end, said leg member extending substantially perpendicularly from said base member; and
   (b) receiving member including at least one aperture arranged and constructed to receive and retain the free end of said leg member, wherein said staple member comprises a blend of at least two polymers, one of said polymers being polyglycolide homopolymer or a copolymer containing at least about 90 mole percent polymerized glycolide, the other of said polymers being polylactide homopolyme or a copolyme containing at least about 85 mole percent polymerized lactide, with the overall blend containing from about 65 to about 85 weight percent polymerized glycolide, the remainder being polymerized lactide, and wherein said receiving member is an absorbable polymer, wherein the surgical staple has a measurable separation strength three weeks after implantation, and wherein the staple member is non-palpable six to ten weeks after implantation.

3. The surgical fastener of claim 2 wherein said absorbable polymer in said receiving member is poly(p-dioxanone).

4. The surgical fastener of claim 2 wherein said blend contains about 65 to 85 weight per cent polyglycolide homopolymer, the remainder being polylactide homopolymer.

5. The surgical fastener of claim 3 wherein said blend contains from about 65 to 85 weight per cent polyglycolide homopolymer, the remainder being polylactide homopolymer.

6. The surgical fastener of claim 1 in the form of a hemostatic ligating clip.

7. The surgical fastener of claim 1 in the form of an anastomotic coupler.

8. The surgical fastener of claim 1 in the form of a fascia closure.

* * * * *

UNITED STATES PATENT AND TRADEMARK OFFICE
CERTIFICATE OF CORRECTION

PATENT NO. : 4,741,337
DATED : 5/3/88
INVENTOR(S) : Carl R. Smith et al.

It is certified that error appears in the above-identified patent and that said Letters Patent is hereby corrected as shown below:

Column 8, line 18

"receiving"

should read

--a receiving--

Column 8, line 25

"homopolyme"

should read

--homopolymer--

Column 8, line 26

"copolyme" should read -- copolymer --.

Signed and Sealed this

Eighth Day of November, 1988

Attest:

DONALD J. QUIGG

Attesting Officer

Commissioner of Patents and Trademarks